US00PP37618P2

(12) United States Plant Patent
Hansen

(10) Patent No.: US PP37,618 P2
(45) Date of Patent: Aug. 18, 2026

(54) ***SEDUM* PLANT NAMED 'Wineberry Delight'**

(50) Latin Name: ***Sedum* hybrid**
Varietal Denomination: Wineberry Delight

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 19/729,004

(22) Filed: Jan. 14, 2026

(51) Int. Cl.
*A01H 5/02* (2018.01)
*A01H 6/32* (2018.01)

(52) U.S. Cl.
USPC ..... Plt./479

(58) Field of Classification Search
USPC ..... Plt./479
CPC ... A01H 5/02; A01H 5/12; A01H 5/00; A01H 6/328; A01H 6/32
See application file for complete search history.

(56) References Cited

U.S. PATENT DOCUMENTS

PP33,781 P2 * 12/2021 Hansen ..... Plt./479

* cited by examiner

*Primary Examiner* — June Hwu

(57) ABSTRACT

A new and distinct ornamental perennial *Sedum* plant named 'Wineberry Delight' is characterized by dense upright mounds of deep-burgundy vertical stems with foliage that is glaucous blue in the spring and develops dark wine-purple that resists powdery mildew and subsequent scaring. The numerous stems are highly branched and resist lodging in the summer heat and rains. Flower buds are rose-colored and opening to light-pink completely covering the top of the plant. The new plant is useful for the landscape in containers, as specimens, or en masse.

2 Drawing Sheets

Botanical designation: *Sedum* hybrid.
Cultivar denomination: 'Wineberry Delight'.

STATEMENT REGARDING PRIOR DISCLOSURES UNDER 37 CFR 1.77(B)(6)

The first offer for sale was on Feb. 1, 2025, on a website operated by Walters Gardens, Inc. Walters Gardens, Inc. obtained the new plant and all information about the new plant from the inventor. No plants of *Sedum* 'Wineberry Delight' have been sold or offered for sale in this country or anywhere in the world nor has any disclosure of the new plant been made more than one year prior to the effective filing date of this application, and such sale or disclosure within one year was either derived directly or indirectly from the inventor and would be a 35 U.S.C. 102(b) exception.

BACKGROUND OF THE INVENTION

The present invention relates to a new and distinct cultivar of *Sedum* plant, botanically known as *Sedum* and hereinafter referred to by the cultivar name 'Wineberry Delight'.

The new plant is a selection of a planned breeding program conducted by the inventor, at a wholesale perennial nursery in Zeeland, Michigan, USA.

The new *Sedum* plant was selected from a self-pollination of the unreleased, unnamed hybrid known only by the breeder code Nov. 19, 2002 as the female parent at a wholesale perennial nursery in Zeeland, Michigan on Aug. 2, 2013. The seeds were collected in the fall of 2013. *Sedum* 'Wineberry Delight' was assigned the breeder code number 13-33-8 to keep it separated from among thousands of other seedlings of this and other crosses when it progressed through the initial trial phase in the fall of 2015. The selected single seedling clone was originally selected for it strong, healthy, dense growth, colorful foliage and flowers.

Asexual reproduction of *Sedum* 'Wineberry Delight' by division at a wholesale perennial nursery in Zeeland, Michigan, USA since October of 2015, and subsequent vegetative shoot tip cuttings has shown that the unique features of this new *Sedum* plant are stable and reproduced true to type in successive generations.

SUMMARY OF THE INVENTION

Plants of *Sedum* 'Wineberry Delight' have not been observed under all possible environmental conditions. The phenotype may vary somewhat with variations in environment such as temperature, available water, fertility and light intensity without, however, any variation in genotype.

The following traits have been repeatedly observed and are determined to comprise the unique characteristics of *Sedum* 'Wineberry Delight' and distinguish it as a new and distinct autumn stonecrop plant unique from all other autumn stonecrop plants known to the inventor:

1. Dense upright mounds with vertical stems;
2. Center stems remain erect throughout the growing season producing full habit;
3. Glaucous blue foliage develops to dark wine-purple coloration and resists powdery mildew and the subsequent scaring;
4. Numerous deep burgundy stems produce dense clusters of rose buds that open to light pink completely cover the mounded plant;

The female parent does not have as dense basal branching and does not retains its upright stems as well through the entire growing season.

The nearest comparison varieties known to the inventor are: 'After Dark' U.S. Plant Pat. No. 35,965, 'Back in Black' U.S. Plant Pat. No. 33,632, 'Black Jack' U.S. Plant Pat. No. 16,736, 'Midnight Velvet' U.S. Plant Pat. No. 35,725, 'Night Embers' U.S. Plant Pat. No. 29,211, 'Strawberry Milkshake' U.S. Plant Pat. No. 35,629, 'Tiramisu' U.S. Plant Pat. No. 33,781, and 'Xenox' U.S. Plant Pat. No. 16,888.

'After Dark' has a slightly smaller habit, the flower buds are darker, and the flowers are darker garnet-colored. 'Back in Black' has broader and darker leaves, the flowers have cream-colored petals, and carpels become deep garnet. 'Black Jack' has larger and darker leaves that are more susceptible to powdery mildew, and the flowers are a darker purplish red. 'Midnight Velvet' has a lower mounded habit with slightly smaller foliage, darker mauve flower buds and petals that are deep rose-colored. 'Night Embers' is slightly taller and narrower in habit with semi-glossy and broader foliage. 'Strawberry Milkshake' has a slightly shorter and broader habit, the flower buds are dark red and flower petals are moderate purplish-red. 'Tiramisu' has a similar habit, flower buds that are lighter purplish-pink with petals a light purplish-pink. 'Xenox' a similar height, but narrower and more open habit with fewer flowers per cyme that cover less of the mound.

BRIEF DESCRIPTION OF THE PHOTOGRAPHS

The photograph of the new plant demonstrates the unique traits and the overall appearance of *Sedum* 'Wineberry Delight'. The colors are as accurate as reasonably possible with color reproductions of this type. Variations in ambient light spectrum, source and direction may cause the appearance of minor variation in color. The plants used in the photograph were three-year-old plants grown in an open, full-sun trial garden at a wholesale perennial nursery in Zeeland, Michigan with supplemental water and fertilizer when needed. No plant growth regulators or pinching have been used.

DETAILED BOTANICAL DESCRIPTION

Figure 1:
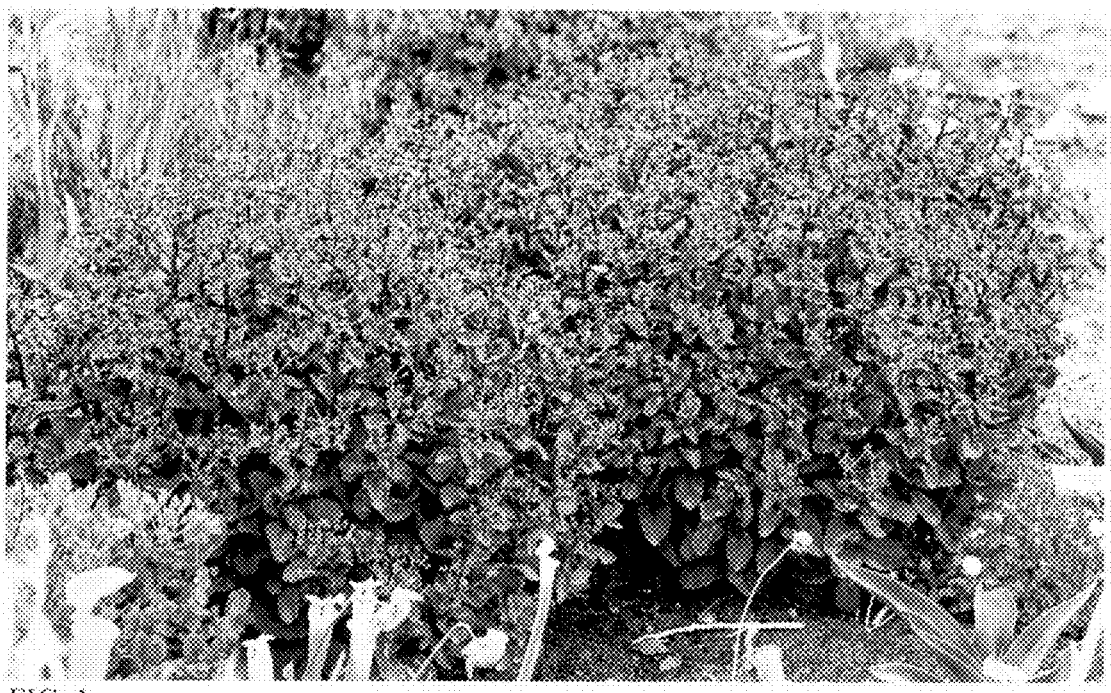
FIG. 1 shows the habit of the new plant with foliage in early stages of flowering.
Figure 2:
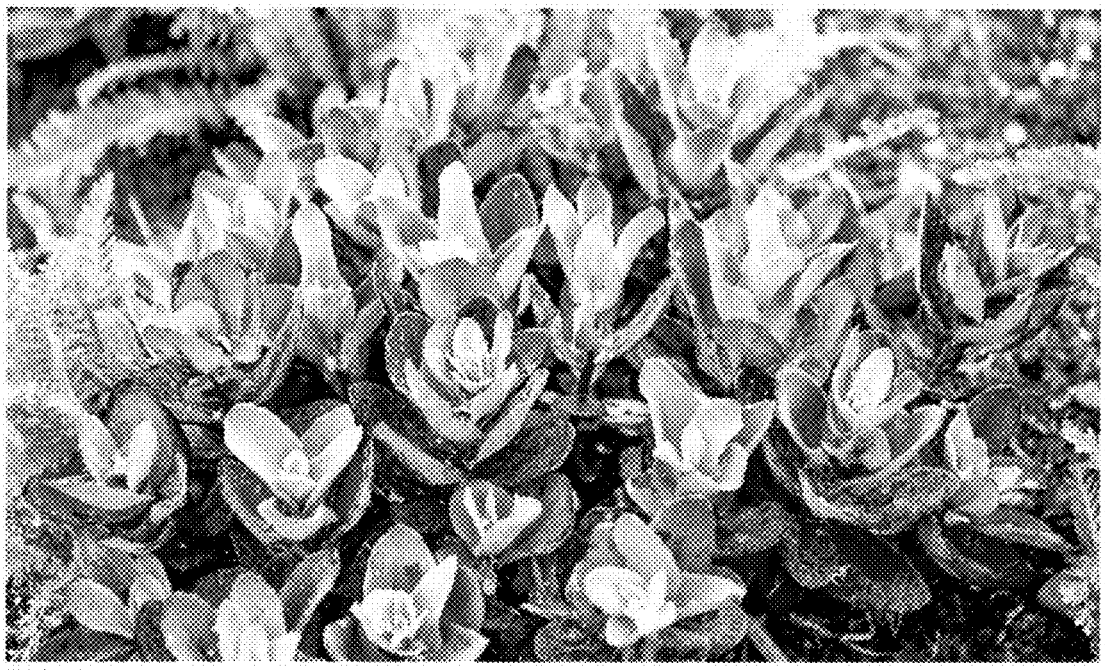
FIG. 2 shows a close-up of the young developing foliage.
Figure 3:
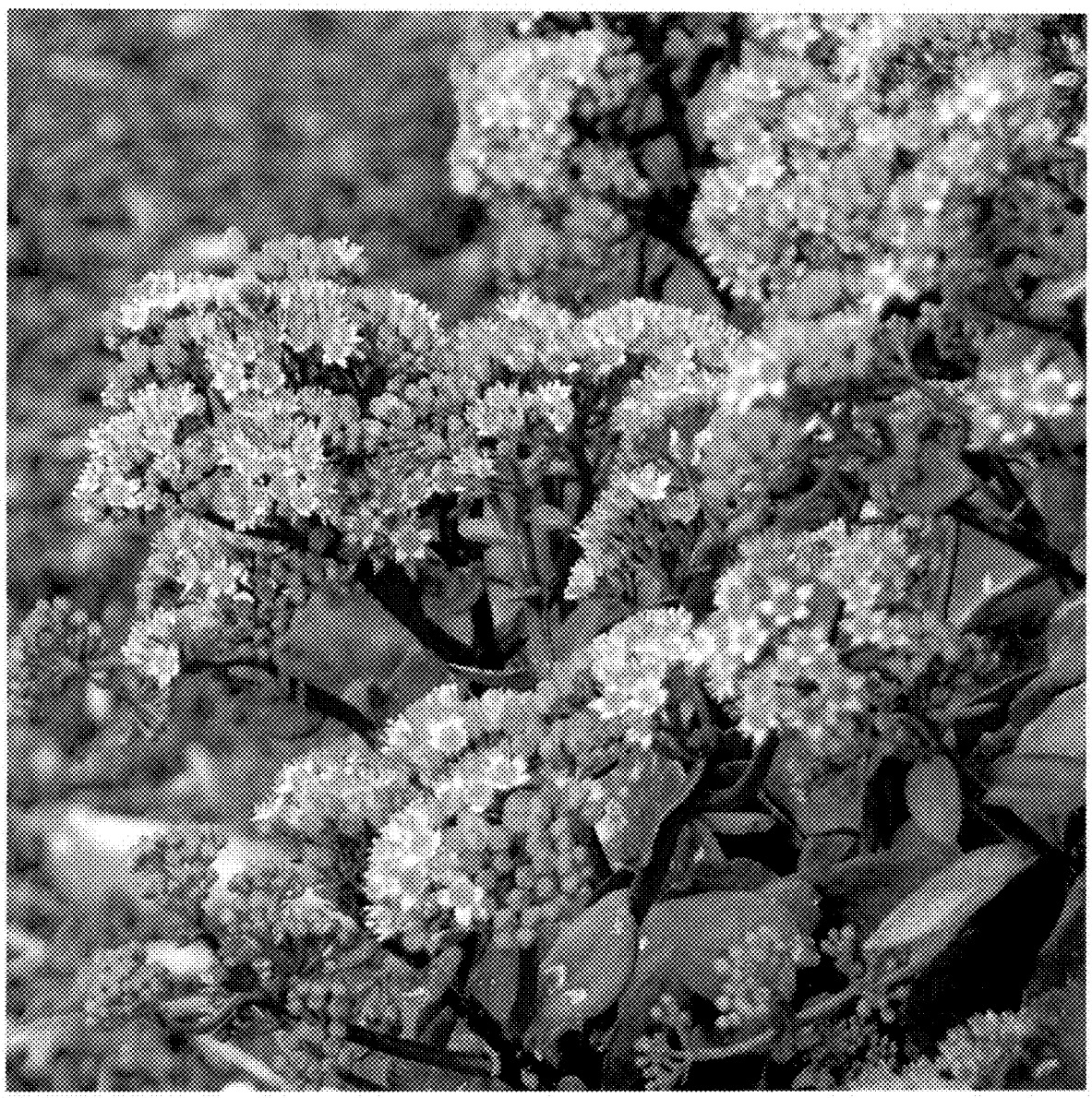
FIG. 3 shows a close-up of the flowers and buds of the new plant in mid-summer.

The following is a detailed description of three-year-old plants of the new cultivar grown outdoors in a full sun trial plot at a wholesale nursery in Zeeland, Michigan. No plant growth regulators have been used. Plants of the new cultivar have not been tested under all possible conditions. The phenotype may vary with changes in the environment, climate, and cultural conditions without change however in the genotype. The color reference is in accordance with the 2015 edition of The Royal Horticultural Society Colour Chart except where general color dictionary terms are used.

Parentage: The parent is Nov. 19, 2002;

Asexual propagation: Stem tip cuttings and division;

Time to initiate roots: About two weeks;

Time to finish a 3.8-liter flowering container: About three months in the summer from a rooted 2.5 cm plug;

Root description: Thick, fleshy; freely branching; creamy white to light tan in color;

Plant habit: Winter-hardy herbaceous perennial; upright mound; stiff upright stems; dense and full, not opening in center later in the season; flower heads freely branching;

Growth rate: Moderately vigorous;

Plant size: About 69 cm tall and 68 cm wide in full flower;

Stems: Cylindrical; glaucous; glabrous; diameter at base to about 10 mm, average about 8.5 mm; heavily branched in distal portion; about 16 cm long from base to initial branches; about 24 stems per plant and 12 to 16 branches per stem;

Stem color: Variable; proximally nearest RHS 146D, maculate with nearest RHS 187C concentrated in portion above leafless nodes; distally between RHS 187A and RHS N187A;

Lateral branches: To about 12 to 16 per stem; glaucous; glabrous; cylindrical; primary branches to about 11 cm long and about 5 mm diameter at base;

Lateral branch color: Between RHS 187C and RHS N187B;

Foliage: Ovate; sinistrorse; flat to slightly calathiform; simple; smooth; sarcous; glabrous and dull on both surfaces; sessile; thick; apex bluntly acute; base rounded to shallowly cordate; margin irregularly and shallowly dentate, 8 to 12 teeth per leaf side, on distal portion; teeth average about 5.0 mm apart; attitude outward; about 19 leaves per stem below branches;

Foliage size: To about 8.3 cm long, 5.6 cm across and 3 mm thick; average about 6.1 cm long, 3.0 cm across and 2 mm thick; decreasing distally;

Foliage color: Young adaxial and abaxial between RHS 122C and RHS 133D; early season developed foliage adaxial between RHS N186D and RHS N77B, abaxial between RHS N186D and RHS N187C; flowering season adaxial in strong light between RHS N77A and RHS N187C, abaxial nearest RHS 148A with an undertone of nearest RHS N77A; flowering season shaded adaxial between RHS 147A and RHS 148A with a moderate blush of nearest RHS 187B, abaxial between RHS 148A and RHS 148B with moderate blush of nearest RHS N77A;

Petiole: Leaves sessile;

Venation: Palmate; glabrous; glaucous; abaxial midrib and primary veins slightly raised;

Vein color: Young adaxial and abaxial proximal midrib nearest RHS N77B and primary veins indistinguishable from surrounding leaf; mature adaxial midrib and distal primary veins nearest RHS 187B, mature abaxial midrib nearest RHS 187C with primary veins variable between RHS 147C and RHS 146C, and nearest RHS 147C with moderate blush of nearest RHS 187C;

Flower: Rotate; actinomorphic; pentamerous; persistent; attitude upright in center portion to outwardly in outer portion of compound cymes; size to about 7 mm across and 5 mm deep;

Flower number: To about 60 to 210 per branch and 700 to 1,000 flowers per stem and 10,000 to 18,000 per plant;

Fragrance: None detected;

Flowering season: Beginning late August in Zeeland, Michigan for about three to four weeks;

Longevity: Flower cymes remain effective for about three to four weeks on the plant and one week as cut flowers; individual flowers and calyces persistent and effective for about three weeks;

Flower buds about one day prior to opening: Ellipsoidal; apex acute; base truncate; about 5 mm long and about 3 mm diameter near middle;

Flower bud color: Distally nearest RHS 59A transitioning just above calyx to between RHS 65D and RHS NN155D; calyx nearest RHS 187A;

Inflorescence: Panicle; to about 21 cm tall from first branch and about 18 cm across;

Petals: Typically five; lanceolate; acute apex; base truncate and fused; margin entire; glabrous abaxial and adaxial; about 3 mm long and about 2 mm across near middle;

Petal color: Young adaxial nearest RHS 64A in distal one-half lightening proximally to nearest RHS NN155D with faint blush of nearest RHS 64A; young abaxial distal one-half nearest RHS 59A and proximally lightening to between RHS 60D and RHS 60C; mature adaxial at apex nearest RHS 61B and proximally nearest RHS N155C; abaxial distal one-third nearest RHS 61A and proximally nearest RHS 186B;

Calyx: With five sepals; campanulate; about 3 mm across and 2 mm deep;

Sepals: Linear to lanceolate; narrowly acute apex; fused in basal 0.5 mm; entire margin; glabrous and slightly glaucous both abaxial and adaxial; adpressed to petals, about 1.5 mm long and about 1 mm across at fusion;

Sepal color: Abaxial and adaxial nearest RHS N187A;

Peduncles: Cylindrical; glaucous, glabrous; stiff and flexible; freely branching; mostly upwardly to slightly outwardly; with branches to about 45° from perpendicular; about 20 cm long and 1.1 mm diameter below first branches;

Peduncle color: Between RHS 187A and RHS N187B;

Pedicels: Cylindrical; glabrous; glaucous; strong and stiff, yet flexible; to about 4 mm long and 1 mm diameter; average about 3 mm long and 0.7 mm diameter;

Pedicel color: Nearest RHS 148B with faint blush of nearest RHS 187B;

Androecium: Ten;

*Filaments*.—Ten, five adnate the lower 1.5 mm of adaxial petals and five attached between petals at the base of the ovaries; cylindrical; glabrous; filaments attached to base of ovary to about 4 mm long and about 0.3 mm diameter, filaments adnate to petals about 3.5 mm long and 0.3 mm diameter; color initially nearest RHS NN155D maturing to between RHS 65D.

*Anther*.—Ten; ellipsoidal; basifixed; longitudinal; about 0.7 mm long and 0.5 mm across; color nearest RHS 26B adaxial and nearest RHS 45A abaxial.

*Pollen*.—Abundant; less than 0.1 mm across; color nearest RHS 18B.

Gynoecium: Typically five; cylindrical, conic in distal one-third; about 3.5 mm long and 1 mm diameter;

*Style*.—Terete; tapering distally and base truncate; about 0.5 mm long and 0.2 mm diameter at point of attachment to ovary; glabrous; lustrous; color nearest RHS 64D to strongly blushed with RHS 64B.

*Stigma*.—Minute, acute; about 0.2 mm diameter and 0.1 mm long; color nearest RHS 64B.

*Ovary*.—Nearly terete; acutely tapering at apex to style; base truncate; lustrous; persistent; about 3 mm long and 1.2 mm diameter; color proximally nearest RHS 39D and distally between RHS 60C and RHS 60D, developing with maturity nearest RHS.

Fruit and seed have not been observed to date.

Growing conditions: Plants of the new *Sedum* 'Wineberry Delight' are xeromorphic and grow best with good drainage, full sun and moderate to low fertility. The new plant is cold hardy from USDA zones 3 to 9 and has tolerated temperatures of at least 35 degrees C. 'Wineberry Delight' tolerates heavy rains and wind and is not prone to develop an open center later in the season as many other *Sedum* cultivars do that are known to the inventor.

Disease and pest resistance: The new plant shows resistance to powdery mildew. Other pest and disease resistance and tolerance outside that normal for *Sedum* is not known to date.

It is claimed:

1. A new and distinct perennial *Sedum* plant named 'Wineberry Delight' as herein described and illustrated.

* * * * *